United States Patent [19]

Hanafusa et al.

[11] Patent Number: 5,377,279
[45] Date of Patent: Dec. 27, 1994

[54] METHOD AND APPARATUS FOR DISPLAYING DEFECT IN CENTRAL AREA OF MONITOR

[75] Inventors: Hideyuki Hanafusa, Takamatsu; Masami Nishio, Kagawa, both of Japan

[73] Assignee: Futec Inc., Takamatsu, Japan

[21] Appl. No.: 946,188

[22] Filed: Sep. 17, 1992

[30] Foreign Application Priority Data

Sep. 19, 1991 [JP] Japan ................... 3-239808

[51] Int. Cl.$^5$ ............ G01N 21/89; G01N 21/86; H04N 7/18
[52] U.S. Cl. ............................. 382/8; 348/88; 348/130; 348/133; 356/430
[58] Field of Search ............ 382/8; 358/106, 101; 356/430, 431, 237; 345/201; 348/86, 88, 92, 125, 128–130, 133, 131

[56] References Cited

U.S. PATENT DOCUMENTS

| | | | |
|---|---|---|---|
| 4,223,346 | 9/1980 | Neiheisel et al. | 358/131 |
| 4,675,730 | 6/1987 | Adomaitis et al. | 358/131 |
| 4,692,943 | 9/1987 | Pietzsch et al. | 382/8 |
| 4,737,846 | 4/1988 | Tokuno et al. | 358/128 |
| 4,979,034 | 12/1990 | Funaki | 358/64 |

FOREIGN PATENT DOCUMENTS

| | | |
|---|---|---|
| 0284630 | 10/1988 | European Pat. Off. |
| 0329889 | 8/1989 | European Pat. Off. |
| 3222753 | 8/1983 | Germany |
| 2081891 | 2/1982 | United Kingdom |
| 2159623 | 12/1985 | United Kingdom |
| 2239946 | 7/1991 | United Kingdom |
| WO91/14173 | 9/1991 | WIPO |
| WO92/08967 | 5/1992 | WIPO |

*Primary Examiner*—Leo H. Boudreau
*Assistant Examiner*—Larry J. Prikockis
*Attorney, Agent, or Firm*—Jacobson, Price, Holman & Stern

[57] ABSTRACT

A method of displaying a defect appearing on an elongated object conveyed in one direction. The method comprises the steps of scanning the object in the width direction thereof by means of a sensor camera, and obtaining object image data corresponding to the object, processing the object image data, to detect a defect in the object, storing the object image data in an image memory in a scroll manner, stopping the scroll storing of the object image data in the image memory and storing the object image data output subsequently from the sensor camera in the other image memory in response to the detection of the defect, and retaining the object image data including the defect in the image memories as still image data, and displaying the still image data read out from the image memories on a monitor screen as a still image such that the defect is displayed at a predetermined position on the monitor screen.

14 Claims, 8 Drawing Sheets

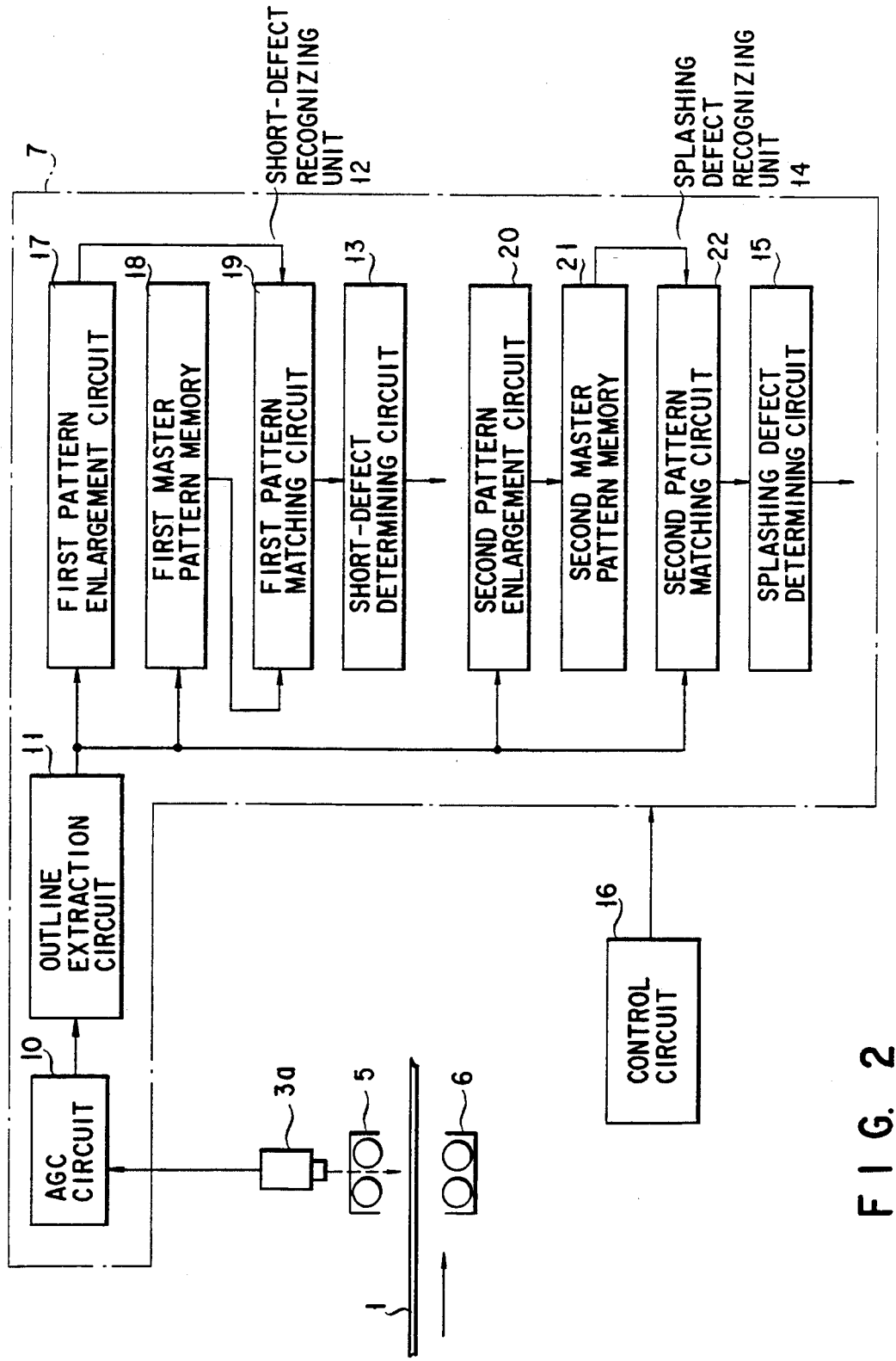
F I G. 2

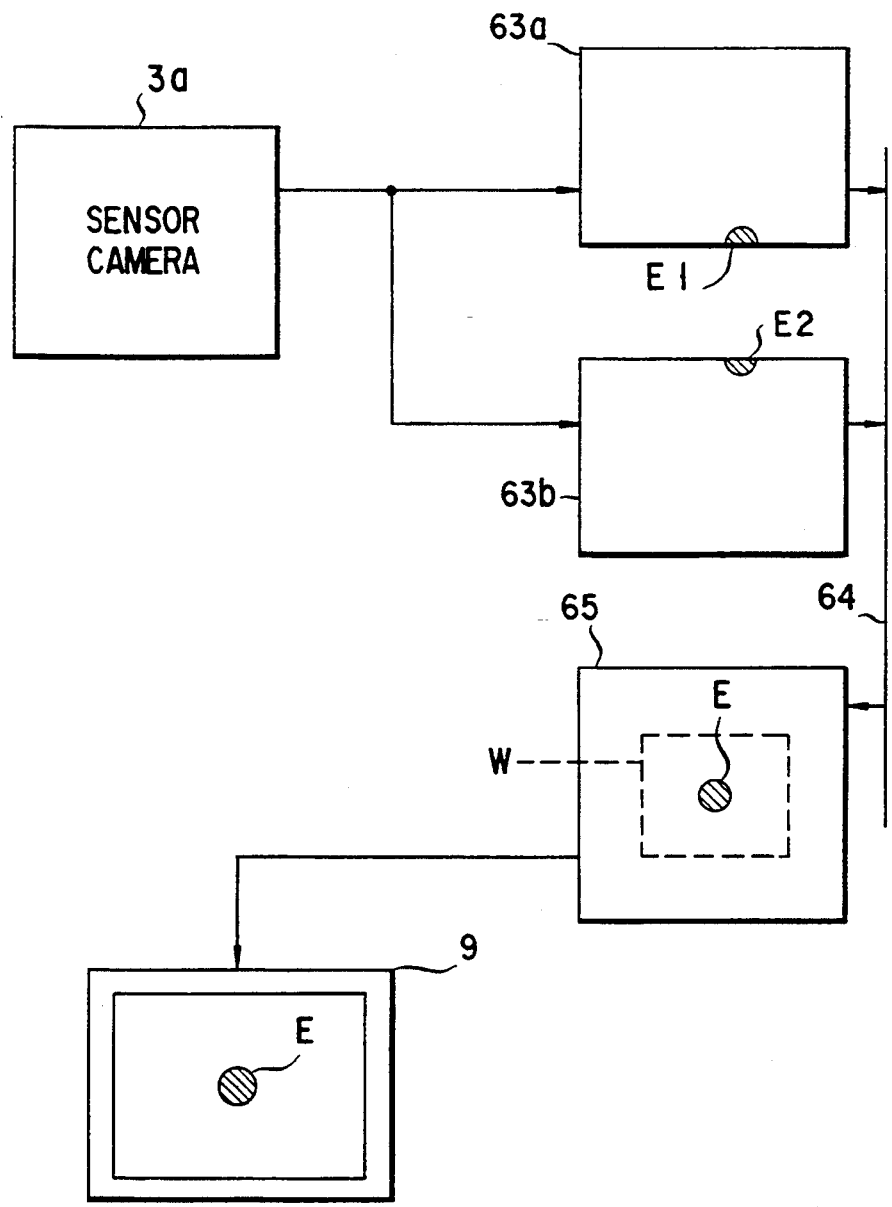
F I G. 11

METHOD AND APPARATUS FOR DISPLAYING DEFECT IN CENTRAL AREA OF MONITOR

BACKGROUND OF THE INVENTION

1. Field of the Invention

The present invention relates to a method for displaying a defect and an apparatus therefor. Specifically, according to this method and apparatus, a defect, which appears on an object having a solid-color surface to be recognized, such as paper, film, metallic foil or nonwoven fabric cloth, or on an object having a printed surface to be recognized, such as a gravure or offset printed matter, is detected and displayed on the screen of a monitor.

2. Description of the Related Art

Displaying a detected defect as a still image on a monitor is advantageous in finding the type and shape of the defect and realizing an early countermeasure to the defect. According to a conventional method of displaying a defect, a camera for scanning an object to be displayed (or a monitor camera) is situated on the downstream side of a defect detecting apparatus (including a sensor camera for detecting a defect) in a direction in which the object is conveyed. The signal from the sensor camera is shifted in accordance with the object convey speed, and the monitor camera scans a defective area on the object, whereby the defect is displayed as a still image on a monitor.

According to this method, the moving object is illuminated at the position of inspection, and, in this state, the object is scanned over its entire width by the defect detection sensor camera comprising a linear array image sensor. An image signal from the sensor camera is processed to determine the good/bad condition of the object. When the recognized image is determined to be defective, the position of the defect in the width direction of the object is found. Subsequently, the monitor color TV camera, which is movable in the width direction of the object and is disposed on the defect monitor position on the downstream side of the inspection position on which the sensor camera is placed, is moved beforehand to the position where the defect will pass, on the basis of the defect position information. When the moving object passes the defect monitor position, the TV camera scans the defect while this defect is illuminated by a strobe light source. The resultant image signal is displayed on the screen of the monitor as a color still image.

In the above conventional method of displaying a defect, the defect is scanned by the defect detection sensor camera while this defect is illuminated by the inspection illumination device. The position and emission wavelength of the inspection illumination device are controlled to emphasize the defect. On the other hand, the monitor color TV camera scans the object while it is illuminated by the strobe light source which is different from the inspection illumination device. The position and emission wavelength of the strobe light source, however, are not controlled to emphasize the defect. In addition, the resolution of the monitor color TV camera is lower than that of the defect detection sensor camera, Thus, in some cases, the defect in the field of view of the monitor color TV camera is not clearly picked up.

Furthermore, a slight slip occurs in a pulse generator for detecting the speed of movement of the object, and there is a concern that the defect in the field of view of the monitor color TV camera may not be picked up exactly. Consequently, the operator is unable to understand the exact area on the screen of the monitor where the defect is displayed and has some difficulty in finding the defect, in particular, when the object is a printed matter.

SUMMARY OF THE INVENTION

An object of the present invention is to provide an apparatus and a method for displaying a defect, wherein the defect display performance on a monitor and visual defect recognizability is enhanced.

According to the invention, there are provided a defect display method and apparatus. In these method and apparatus, a conveyed object is illuminated at the inspection position. While being illuminated, the object is scanned in the width direction thereof by a sensor camera constituted by a linear array image sensor. An image signal from the sensor camera is input to both a defect detecting device for detecting a defect on the object and a defect image processing device for generating image data including data on the defect detected by the defect detecting device. On the basis of the defect detection by the defect detecting device, the image data containing the defect is displayed on a monitor as a still image. The defect in the still image is displayed at a vertically middle point ($\frac{1}{2}$ height position) on the screen of the monitor.

In addition, according to the invention, there are provided a defect display method and apparatus. In these method and apparatus, a conveyed object is illuminated at the inspection position. While being illuminated, the object is scanned in the width direction thereof by sensor cameras constituted by a linear array image sensor. Image signals from the sensor cameras are scroll-recorded in image memories provided for the respective cameras and each having a memory capacity equal to half the memory capacity of a display buffer memory. In parallel with the data recording, when a defect detecting device for processing the image signals from the sensor cameras detects a defect on the object, the write-in of data in the image memory corresponding to the sensor camera which scans the defect is stopped. Thereafter, image signals from the sensor camera which scans the defect are stored in another image memory having a memory capacity equal to half the capacity of the display buffer memory. Subsequently, half-frame image data containing a half part of the defect and stored in the image memory and half-frame image data containing the other half part of the defect and stored in said another image memory are transferred sequentially to the display buffer memory. These transferred half-frame image data are synthesized in the display buffer memory. The synthetic image is displayed on the monitor as a still image.

In this invention, the defect image processing device for generating image data including the defect detected by the defect detecting device receives the same signal as the input signal to the defect detecting device, i.e. the image signal from the sensor cameras constituted by the linear array image sensor. The sensor cameras scan the object while it is illuminated. In this manner, the lighting devices and sensor cameras designed in consideration of the position and wavelength capable of emphasizing the defect are used for both the defect detecting device and defect image processing device. Thus, the resolution of the lighting devices is consistent with the resolution of the cameras. In addition, when the defect data is displayed on the monitor, the defect is displayed at the vertically middle point (½ height position) on the screen of the monitor. Thus, the display position of the defect is stabilized.

In the present invention, the sensor cameras scan the object in the width direction thereof while it is illuminated at the inspection position. Image signals from the cameras are input to the image memories provided for the respective cameras, and to the defect detecting device. Thus, there is consistency in resolution between the lighting devices and the cameras in both defect detection and defect display operations.

The image memories store the image signals from the corresponding cameras in a scroll manner, and each has a memory capacity equal to half the capacity of the display buffer memory. The scroll operation of the image memories is stopped when the defect detecting device detects the defect. At the time the write-in is stopped, the image memory has already stored image data containing part of the defect, and another image memory stores subsequent image signals output from the sensor camera which has detected the defect. The image data stored in the another image memory contains the other part of the defect. The data stored in the image memories are transferred to the display buffer memory. Then, the buffer memory synthesizes the transferred data from both image memories, and the synthetic image is displayed on the monitor as a still image. The defect is stably displayed at the vertically middle point on the screen of the monitor.

According to the present invention, there is provided a defect detecting device wherein the object image data is processed to emphasize a defect candidate, the image signal corresponding to the defect candidate is compared with a predetermined signal level and parameters corresponding to a predetermined width and a predetermined length, and the defect candidate is recognized as a defect when the defect image signal exceeds the signal level and the parameters.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute apart of the specification, illustrate presently preferred embodiments of the invention, and together with the general description given above and the detailed description of the preferred embodiments given below, serve to explain the principles of the invention.

FIG. 2 is a block circuit diagram of a defect detection apparatus;

FIG. 11 is a view for describing the operation of the defect display apparatus shown in FIG. 1.

DETAILED DESCRIPTION OF THE PREFERRED EMBODIMENTS

Figure 1:
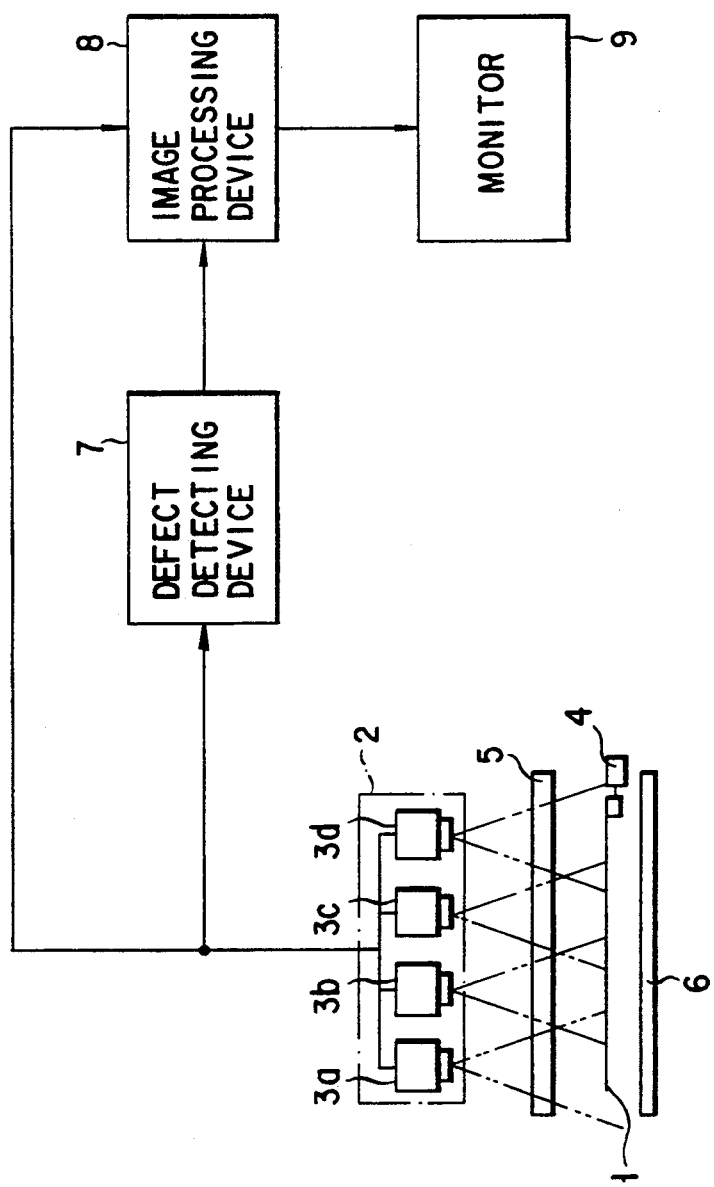
FIG. 1 is a block diagram showing an example of the circuit configuration of a defect display apparatus by which a defect display method according to the present invention is worked.

According to a defect display apparatus shown in FIG. 1, a to-be-recognized object 1 is, for example, a continuous long printed matter or a continuous long matter without a pattern. The object 1 is moved in a direction vertical to the surface of the drawing sheet of FIG. 1. A camera unit 2 is situated at a desired inspection position in relation to the direction of movement of the object 1. The camera unit 2 comprises, for example, four defect detection sensor cameras 3a to d which are situated to face the upper surface (to-be-inspected surface) of the object 1.

A pulse generator 4 is rotatably put in contact with an edge portion of the object 1 or a rotary portion of a driving mechanism for moving the object 1. The pulse generator 4 is employed to obtain positional information of the object 1.

A first lighting device 5 facing the upper surface of the object 1 and a second lighting device 6 facing the bottom surface of the object 1 are arranged at the inspection position. Either or both of the lighting devices 5 and 6 are turned on, depending on the quality, etc. of the object 1, thereby lighting the field of view of the cameras 3a to 3d and emitting light of wavelength necessary for emphasizing the defect to the object 1 in a specified direction.

Each of the sensor cameras 3a to 3d is constituted by a CCD linear array image sensor. The printed surface of the object 1 is scanned over the entire width thereof by the cameras 3a to 3d. Image signals output from the cameras 3a to 3d are delivered to a defect detecting device 7 and a defect image processing device 8. An output terminal of the device 8 is connected to a monitor 9. The defect detecting device 7 processes the object image data to detect a defect, and outputs a defect detection signal when the image signal corresponding to the defect exceeds a predetermined signal level and parameters corresponding to a predetermined width and a predetermined length.

FIG. 2 shows the structure of the defect detecting device 7 suitable for detecting a defect on a printed matter.

In FIG. 2, the field of view of the sensor cameras a to 3d facing the surface of the object 1 conveyed in the direction of an arrow is illuminated by the first lighting device 5 and/or second lighting device 6.

The sensor cameras 3a to 3d scan the surface on the object 1 in a direction perpendicular to the direction in which the object 1 is conveyed. Image data output from the cameras 3a to 3d is input to a defect detecting device 7. The defect detecting device 7 detects a defect such as print defect, spot, stain or smudge on the surface of the object 1.

The defect detecting device 7 comprises an AGC circuit 10, an outline extraction circuit 11, a short-defect recognizing unit 12, a short-defect determining circuit 13, a splashing defect recognizing unit 14, a splashing defect determining circuit 15, and a control circuit 16.

The AGC circuit 10 is connected to the output terminals of the sensor cameras 3a to 3d. The AGC circuit 10 stabilizes a gain variation of the entire defect detecting device 7 and produces a constant transmission output. The outline extraction circuit 11 is connected to an output terminal of the AGC circuit 10. As will be described below, the outline extraction circuit 11 receives all signals from the sensor cameras 3a to 3d, emphasizes a variation of these signals, and extracts image outline data.

The short-defect recognizing unit 12 comprises a first pattern enlargement circuit 17, a first master pattern memory 18 and a first pattern matching circuit 19. The first pattern enlargement circuit 17 is connected to an output terminal of the outline extraction circuit 11. The first pattern enlargement circuit 17 enlargement-processes data relating to outline in a vertical direction and in a horizontal direction, thereby making allowable a certain variation in printed patterns on the object 1 and a certain error in precision of conveyance of the object 1 (e.g. precision of conveyance by a conveyor for conveying the object 1). Thus, a slight initial variation in patterns and a slight error in precision of conveyance of the object 1 can be ignored. The degree of enlargement is set at the initial setting time. The first pattern enlargement circuit 17 enlargement-processes image data corresponding to the outline and forms a to-be-recognized pattern. The details of outline extraction circuit 11 and pattern enlargement circuit 17 will be described later.

The first master pattern memory 18 is a writable/readable memory connected to the output terminal of the outline extraction circuit 11. The pattern memory 18 stores master outline data extracted by the output extraction circuit 11 from a printed matter which has been determined to be free of defects by the naked eye or other means. The memory 18 maintains the stored master outline data while the same kind of printed matters are being checked.

The first pattern matching circuit 19 is connected to an output terminal of the first pattern enlargement circuit 17 and an output terminal of the first master pattern memory 18. The matching circuit 19 compares to-be-recognized pattern data obtained by the first pattern enlargement circuit 17 with the master outline data read out of the first master pattern memory 18, and determines whether the pattern data matches with the master outline data.

The short-defect determining circuit 13 is connected to an output terminal of the first pattern matching circuit 19. The short-defect determining circuit 13 checks the size represented by the defect data obtained by the short-defect recognizing unit 12 and determines whether or not the detected defect is a short-defect. The size of the defect is set in the short-defect determining circuit 13 at the time of initial setting.

Figure 4:
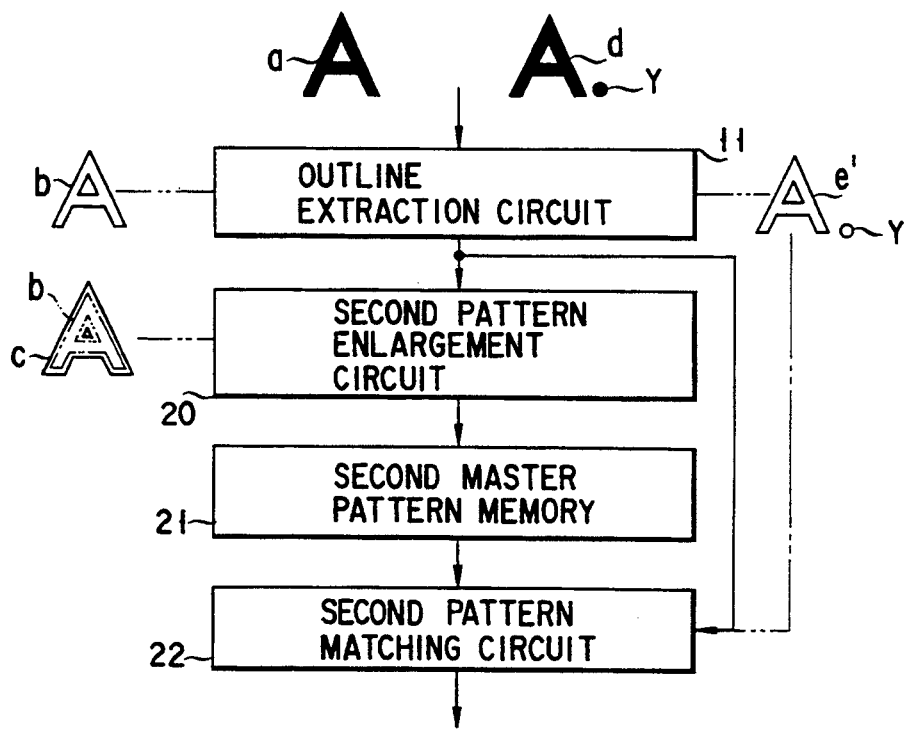
FIG. 4 is a block circuit diagram of a splashing defect recognizing unit shown in FIG. 2.

The splashing defect recognizing unit 14, as shown in FIGS. 2 and 4, comprises a second pattern enlargement circuit 20, a second master pattern memory 21 and a second pattern matching circuit 22.

The second pattern enlargement circuit 20 is connected to the output terminal of the outline extraction circuit 11. The second pattern enlargement circuit 20 has the same structure as the first pattern enlargement circuit 17, and it expands the outline data to enlarge the image outline, thus producing master enlarged pattern data.

The second master pattern memory 21 is connected to an output terminal of the second pattern enlargement circuit 20. The second master pattern memory 21 is a writable/readable memory. The pattern memory 21 stores master enlarged pattern data which is extracted from a printed matter which has been determined to be free of defects by the naked eye or other means, and which is capable of being processed by the second pattern enlargement circuit 20. The memory 21 maintains the stored master enlarged pattern data while the same kind of printed matters or objects 1 are being checked.

The second pattern matching circuit 22 is connected to the output terminal of the outline extraction circuit 11 and an output terminal of the second master pattern memory 21. The second pattern matching circuit 22 compares the outline data on the object 1 obtained by the outline extraction circuit 11 with the master enlarged pattern data read out of the second master pattern memory 21, and determines whether the outline data matches with the pattern data.

The splashing defect determining circuit 15 is connected to an output terminal of the second pattern matching circuit. The splashing defect determining circuit 15 checks the size represented by the defect data obtained by the splashing defect recognizing unit 14 and determines whether or not the defect is a splashing defect. The Size of the defect is set in the splashing defect determining circuit 15 at the time of initial setting.

The control circuit 16 controls the AGC circuit 10, outline extraction circuit 11, short-defect recognizing unit 12, short-defect determining circuit 13, splashing defect recognizing unit 14 and splashing defect determining circuit 15.

The defect-detecting operation of the apparatus with the above structure will now be described.

After the initial setting operation is completed, the printed pattern on the object, which has been determined to be free of defects by the naked eye or other means, is scanned by the sensor cameras 3a to 3d and outline data is extracted from the image data relating to the defect-free object (master) by the outline extraction circuit 11. The extracted outline data is stored in the short-defect recognizing unit 12 and splashing defect recognizing unit 14, as shown in FIGS. 3 and 4.

Figure 3:
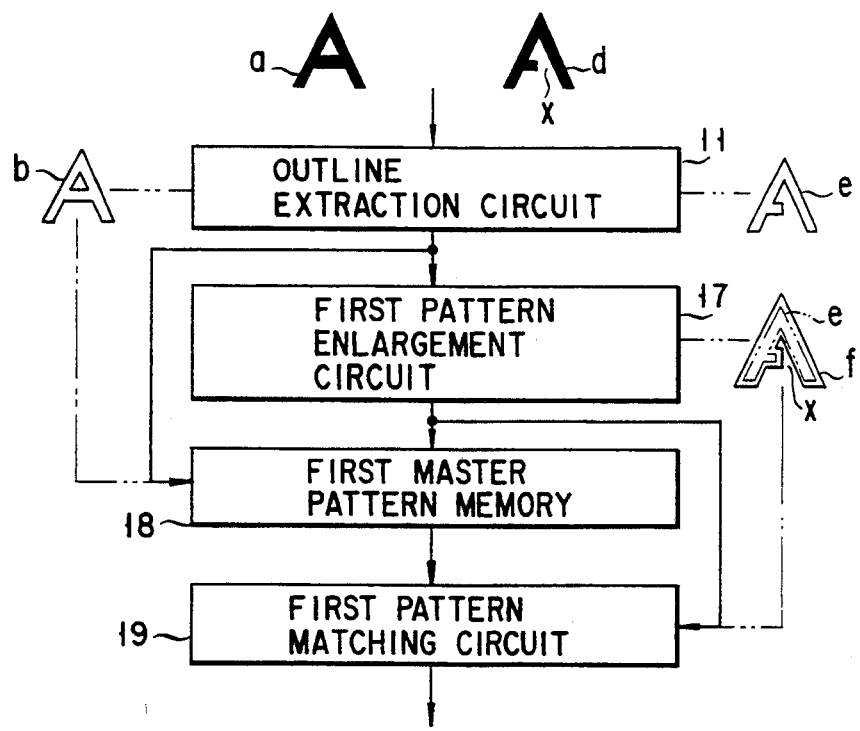
FIG. 3 is a block circuit diagram of a short-defect recognizing unit shown in FIG. 2.

Specifically, in the short-defect recognizing unit 12, master image data indicated by symbol a in FIG. 3 (e.g. outline data (b) of letter A) which has been output from the outline extraction circuit 11 is stored in the first master pattern memory 18 as master outline data. In the splashing defect recognizing unit 14, outline data (b) of master pattern A indicated by symbol a in FIG. 4, which has been output from the outline extraction circuit 11, is expanded by the second pattern enlargement circuit 20 and the obtained data of the master enlarged pattern (c) is stored in the second master pattern memory After the master pattern is set, the object 1 is moved into the field of view of the sensor cameras 3a to 3d and is scanned. Defect (d) data output from each of the sensor cameras 3a to 3d is input to the outline extraction circuit 11 via the AGC circuit 10. Then, outline (e) data is extracted from the pattern (d) data by the outline extraction circuit 11. The outline (e) data is input to the short-defect recognizing unit 12 and splashing defect recognizing unit 14.

As is shown in FIG. 3, in the short-defect recognizing unit 12, the outline (e) data relating to the object 1 output from the outline extraction circuit 11 is expanded by the first pattern enlargement circuit 17. To-be-recognized pattern (f) data obtained by the enlargement step is delivered to the first pattern matching circuit 19. The input of the to-be-recognized (f) data to the circuit 19 is performed simultaneously with reading-out of the master outline (b) data relating to the master pattern A from the first master pattern memory 18 to the first pattern matching circuit 19. Thereby, both data elements are compared and matched.

If the image d has a short-defect X (this defect X is larger than an enlargement size set in the enlargement circuit 17) as shown in FIG. 3, a portion of the outline d corresponding to the master pattern projects from the enlarged to-be-recognized pattern f. The first pattern matching circuit 19 recognizes this projecting portion as short-defect data.

This defect data is supplied to the short-defect determining circuit 13, and the circuit 13 determines whether the defect represented by the defect data is a true defect. This determination is performed by checking whether or not the defect represented by the input defect data has a size greater than a predetermined size.

The outline (e) data of pattern (d) of object 1 supplied to the splashing defect recognizing unit 14 is not expanded and is directly supplied to the second pattern matching circuit 22. The outline (e') data of object 1 is input to the circuit 22 simultaneously with reading-out of master enlarged pattern (c) data relating to the master image A from the second master pattern memory 21 to the second pattern matching circuit 22. Thus, both pattern data elements are compared and matched.

If the image d has a splashing defect Y as shown in FIG. 4, a portion of an outline e' corresponding to the object 1 projects from the enlarged master pattern c. The second pattern matching circuit 22 recognizes this projecting portion as splashing defect. The defect data corresponding the splashing defect is supplied to the splashing defect determining circuit 15, and the circuit 15 determines whether the defect represented by the defect data is a true defect. Like the aforementioned short defect, this determination is performed by checking whether or not the defect represented by the input defect data has a size greater than a predetermined size.

The short-defect recognizing unit 12 and splashing defect recognizing unit 14 will now be described in greater detail with reference to FIGS. 5 and 6.

Figure 5:
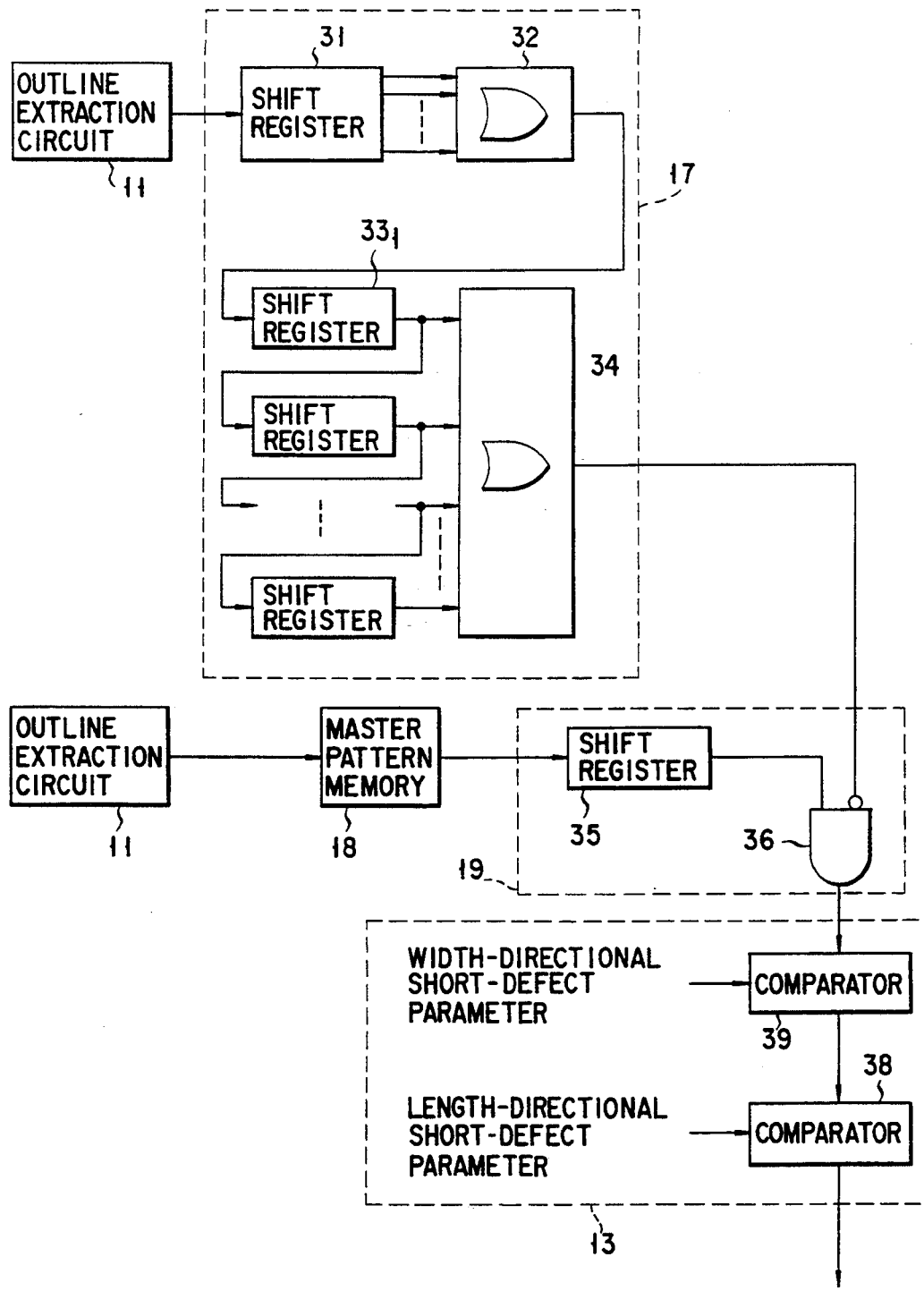
FIG. 5 is a circuit diagram of the short-defect recognizing unit shown in FIG. 3.

As is shown in FIG. 5, the first pattern enlargement circuit 17 of the short-defect recognizing unit 12 comprises a width-directional enlargement circuit and a length-directional enlargement circuit. The width-directional enlargement circuit comprises a shift register 31 connected to an output terminal of the outline extraction circuit 11 for extracting the outline of the printed pattern from the printed pattern image signal, and an OR gate 32 having input terminals connected to the output terminals of the shift register 31. The length-directional enlargement circuit comprises a shift registers $33_1$ to $33_n$ including a first-stage shift register $33_1$ connected to the output terminal of the OR gate 32, and an OR gate 34 having input terminals connected to the output terminals of these shift registers.

The first pattern matching circuit 19 comprises a shift register 35 connected to a read-out terminal of the first master pattern memory 18 for storing the master pattern extracted by the outline extraction circuit 11, and an AND gate 36 having a non-inversion input terminal connected to the output terminal of the shift register 35 and an inversion terminal connected to the output terminal of the first pattern enlargement circuit 17 (i.e. the output terminal of the OR gate 34).

The short-defect determining circuit 13 comprises a width-directional defect determining comparator 37 having a first input terminal connected to the output terminal of the first pattern matching circuit 19 (i.e. the output terminal of the AND gate 36) and a second input terminal supplied with a width-directional defect parameter, and a length-directional defect determining comparator 38 having a first input terminal connected to the output terminal of the comparator 37 and a second input terminal supplied with a length-directional defect parameter.

The operation of the short-defect recognizing unit 12 will now be described.

Outline pattern (a) data is input from the outline extraction circuit 11 to the shift register 31. The outline pattern data stored in the shift register 31 is read out with such a timing that the data is enlarged in the pattern width direction in accordance with a width-directional enlargement parameter. The read-out width-directional enlargement pattern data is fed to the shift registers $33_1$ to $33_n$ via the OR gate 32 and retained in these shift registers on a line-by-line basis. The pattern data retained in the shift registers $33_1$ to $33_n$ is read out with such a timing that the data is enlarged in the length direction in accordance with a length-directional enlargement parameter. The read-out data is fed to the OR gate 34.

The width- and length-directional enlargement pattern data output from the OR gate 34 is input to the inversion input terminal of the AND gate 36 of the first matching circuit 19. The output data from the shift register 35 is input to the non-inversion input terminal of the AND gate 36. The shift register 35 retains the master pattern data read out from the master pattern memory 18 and outputs the master pattern data to the AND gate 36 with such a timing that the center of the master pattern represented by the master pattern data coincides with the center of the enlargement pattern of the enlargement pattern data input from the first pattern enlargement circuit 17. Accordingly, the AND gate 36 compares the master pattern data with the enlargement pattern data, and outputs a signal only when the enlargement pattern data is absent and the master pattern is present.

The output signal from the first pattern matching circuit 19 (i.e. the output signal from the AND gate 36) is input to the width-directional defect determining comparator 37 and length-directional defect determining comparator 38 of the short-defect determining circuit 13, whereby the input data is compared with the width- and length-directional defect parameters. When the defect signal from the first pattern matching circuit 19 exceeds the set values (i.e. defect parameters) in both width- and length-directions, the short-defect determining circuit 13 outputs a short-defect determination signal.

Figure 6:
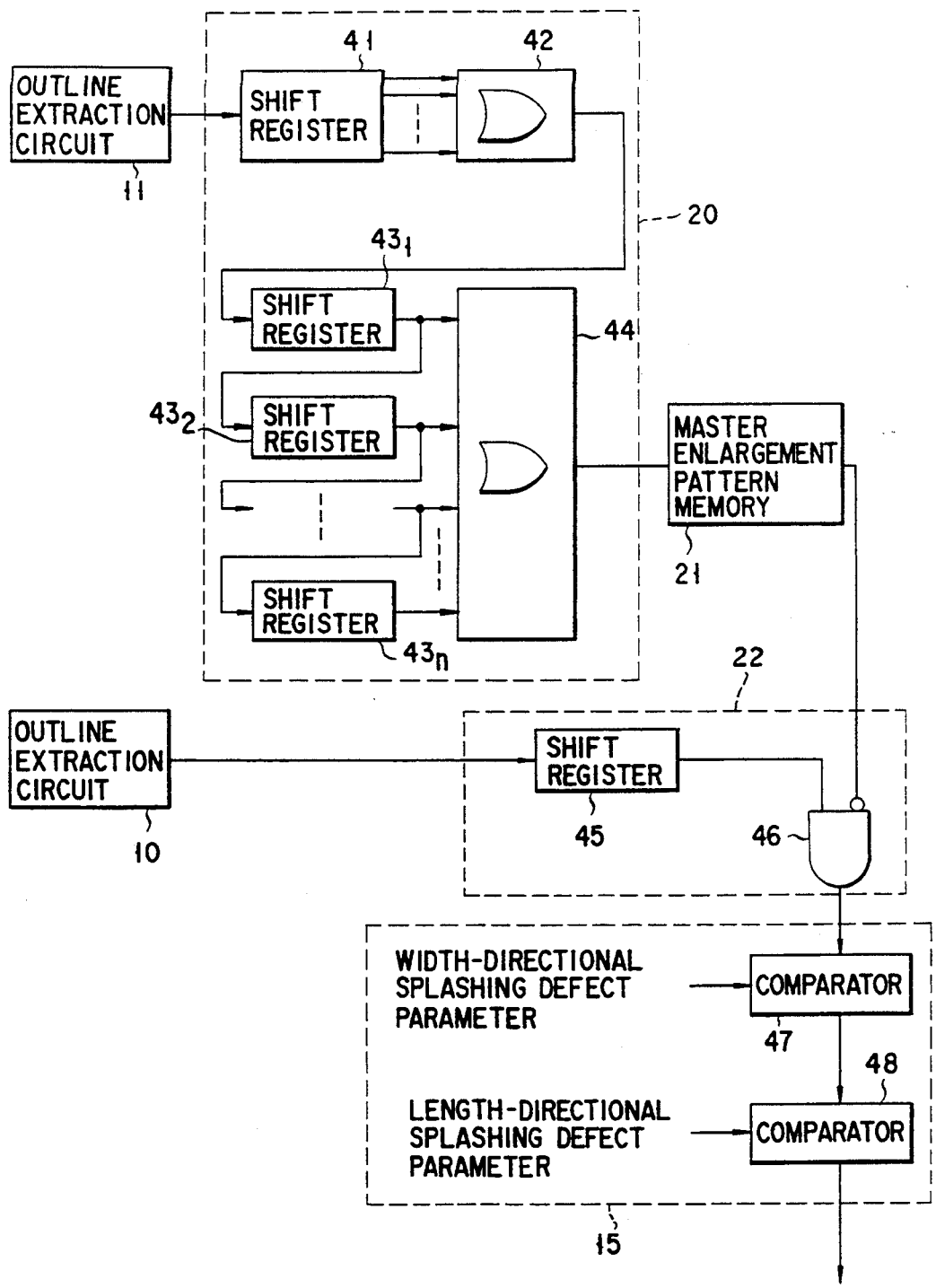
FIG. 6 is a circuit diagram of the splashing defect recognizing unit shown in FIG. 4.

As is shown in FIG. 6, the second pattern enlargement circuit 20 of the splashing defect recognizing unit 14 comprises a width-directional enlargement circuit and a length-directional enlargement circuit. The width-directional enlargement circuit comprises a shift register 41 connected to an output terminal of the outline extraction circuit 1, and an OR gate 42 having input terminals connected to the output terminals of the shift register 41. The length-directional enlargement circuit comprises a shift registers $43_1$ to $43_n$ including a first-stage shift register $43_1$ connected to the output terminal of the OR gate 42, and an OR gate 44 having input terminals connected to the output terminals of these shift registers. The output terminal of the OR gate 44 is connected to the input terminal of the master enlargement pattern memory 21.

The second pattern matching circuit 22 comprises a shift register 45 connected to the outline extraction circuit 11, and an AND gate 46 having a non-inversion input terminal connected to the output terminal of the shift register 45 and an inversion input terminal connected to the output terminal of the master enlargement pattern memory 21.

The splashing defect determining circuit 15 comprises a width-directional defect determining comparator 47 having a first input terminal connected to the output terminal of the second pattern matching circuit 22 (i.e. the output terminal of the AND gate 46) and a second input terminal supplied with a width-directional splashing defect parameter, and a length-directional defect determining comparator 48 having a first input terminal connected to the output terminal of the comparator 47 and a second input terminal supplied with a length-directional splashing defect parameter.

The operation of the splashing defect recognizing unit 14 will now be described.

Master outline (b) data is input from the outline extraction circuit 11 to the shift register 41. The outline data stored in the shift register 41 is read out with such a timing that the outline is enlarged in the pattern width direction in accordance with a width-directional enlargement parameter. The read-out width-directional enlargement pattern data is fed to the shift registers $43_1$ to $43_n$ and retained in these shift registers on a line-by-line basis. The master pattern data retained in the shift registers $43_1$ to $43_n$ is read out with such a timing that the master pattern is enlarged in the length direction in accordance with a length-directional enlargement parameter. The read-out data is fed to the OR gate 44.

The width- and length-directional enlargement pattern data output from the OR gate 44 is stored in the master enlargement pattern memory 21. The master enlargement pattern data read out from the memory 21 is input to the inversion input terminal of the AND gate 46 of the second matching circuit 22. The output data from the shift register 45 is input to the non-inversion input terminal of the AND gate 46. The shift register 45 retains the outline pattern data extracted by the outline extraction circuit 11 and outputs the outline pattern data to the AND gate 46 with such a timing that the center of the outline pattern represented by the outline pattern data coincides with the center of the master enlargement pattern of the master enlargement pattern data read out from the master enlargement pattern memory 21. Accordingly, the AND gate 46 compares the outline pattern data with the master enlargement pattern data, and outputs a signal only when the master enlargement pattern data is absent and the outline data is present.

The output signal from the second pattern matching circuit 22 (i.e. the output signal from the AND gate 46) is input to the width-directional defect determining comparator 47 and length-directional defect determining comparator 48 of the splashing defect determining circuit 15, whereby the input data is compared with the width-directional splashing defect parameter and length-directional splashing defect parameters. When the splashing defect signal from the second pattern matching circuit 22 exceeds the set values (i.e. defect parameters) in both width- and length-directions, the splashing defect determining circuit 15 outputs a splashing defect determination signal.

The structure of the outline extraction circuit 11 and the outline extraction operation will now be described with reference to FIG. 7.

Figure 7:
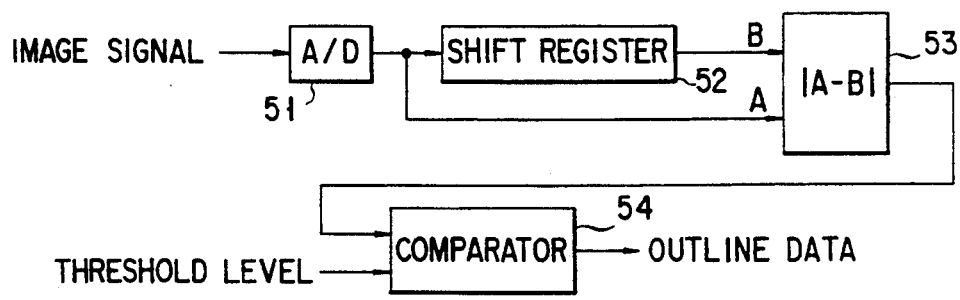
FIG. 7 shows a circuit configuration an outline extraction circuit.

The outline extraction circuit 11, as shown in FIG. 7, comprises an A/D converter 51 for converting an image signal obtained by the AGC circuit 10 to a digital signal, a shift register 52 having an input terminal connected to the output terminal of the A/D converter 51, an absolute value extraction circuit 53 having first and second input terminals connected to the output terminals of the A/D converter 51 and shift register 52, and a comparator 54 having a first input terminal connected to the output terminal of the absolute value extraction circuit 53 and a second input terminal supplied with a threshold level.

Figure 8:
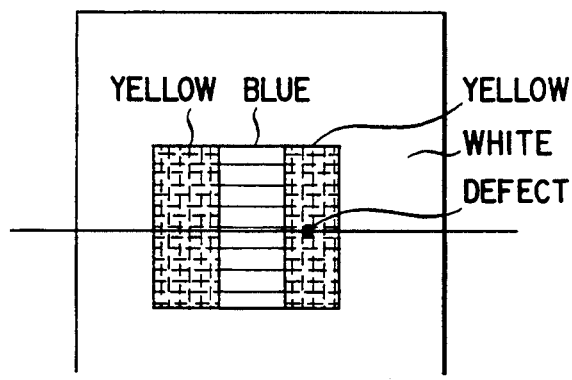
FIG. 8 shows a multicolor print pattern.
Figure 9:
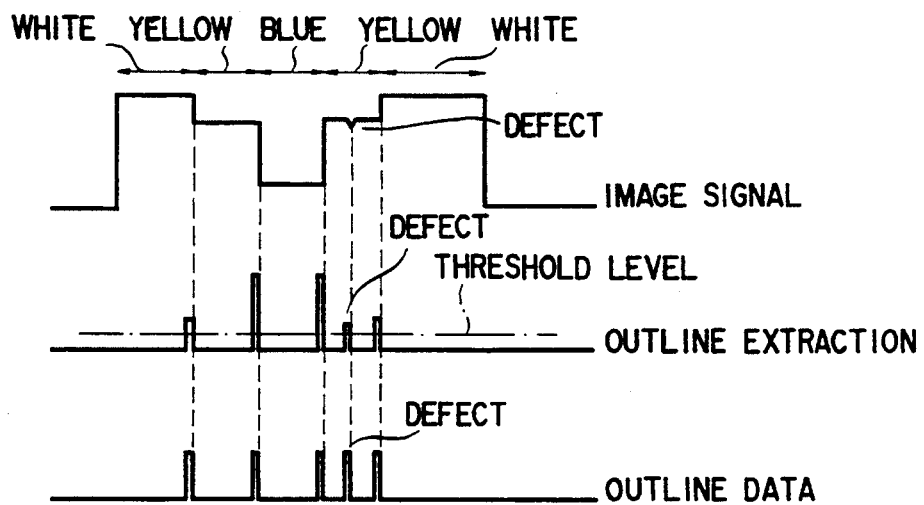
FIG. 9 is a view for describing outline extraction.

For example, a multicolor printed pattern, as shown in FIG. 8, is scanned by the sensor camera 3a of the pattern matching apparatus including the outline extraction circuit 11. A one-line image signal, as shown in FIG. 9, is generated in every line scan and input to the A/D converter 51 of the outline extraction circuit 11. The A/D converter 51 converts the image signal to a digital image signal A and delivers the digital image signal A to the shift register 52 and absolute value extraction circuit 53. The shift register 52 delays the digital image signal A by a predetermined time and delivers the delayed digital signal B to the absolute value extraction circuit 53. Thereby, the absolute value extraction circuit 53 outputs to the comparator 54 an absolute value of a difference between the non-delayed digital signal A and delayed digital signal B. The comparator 54 compares the absolute value with the threshold level, as shown in FIG. 9, and delivers the comparison result, as outline data, to the first pattern enlargement circuit 17, first master pattern memory 18, second pattern enlargement circuit 20 and second pattern matching circuit 22. Then, when the to-be-recognized outline data including the defect data shown in FIG. 9 is matched with reference outline data, it is determined that the to-be-recognized outline data is defect data.

Figure 10:
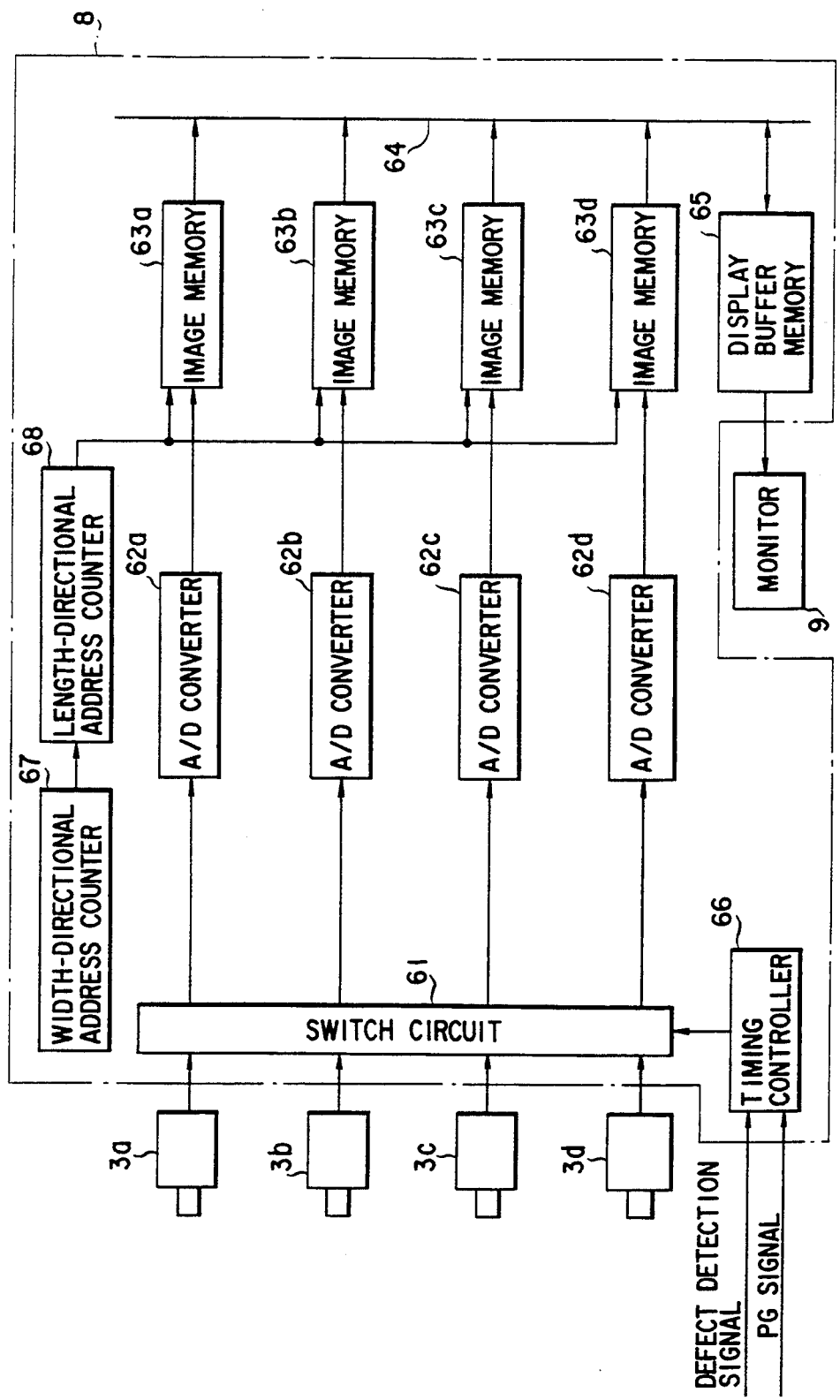
FIG. 10 shows a circuit configuration of a defect image processing circuit.

A defect detection signal produced by the defect detecting device 7 is input to the defect image processing device 8. FIG. 10 shows the structure of the processing device 8.

Referring to FIG. 10, the output terminals of the sensor cameras 3a to 3d are connected to a switch circuit 61 for switching, e.g. analog signals. The output terminals of the sensor cameras 3a to 3d are connected to A/D converters 62a to 62d via the switch circuit 61. The output terminals of the A/D converters 62a to 62d are connected to image memories 63a to 63d provided for the respective sensor cameras 3a to 3d. The output terminals of the image memories 63a to 63d are connected to a display buffer memory 65 via a bus line 64. The output terminal of the buffer memory 65 is connected to a monitor 9.

Normally, the switch circuit 61 inputs image signals from the sensor cameras 3a to 3d to the corresponding image memories 63a to 63d via the A/D converters 62a to 62d. However, when any of the cameras scans a defect, an image signal relating to the defect is input by the switch circuit 61 to another alternative memory, which does not correspond to this camera, via the A/D converter.

This switching is effected by a timing controller 66 which receives a defect detection signal from the defect detecting device 7 and a PG signal (position data) from the pulse generator 4. In this case, the switch circuit 61 effects a switching operation in response to the input of the defect signal and completion of one line scanning. In this embodiment, the image memory selected by the switching operation is a memory neighboring the memory corresponding to the camera which scans the defect. For example, when the sensor camera 3a scans a defect, the image memory 63b neighboring the image memory 63b corresponding to the camera 3a is selected. The image memory 63c is the alternative memory neighboring the image memory 63b, the image memory 63d is the alternative memory to the image memory 63c, and the image memory 63a is to the image memory 63d. It is also possible to provide an exclusive-use memory as alternative memory, in addition to the image memories corresponding to the sensor cameras 3a to 3d.

The memory capacity of each of the image memories 63a to 63d is half the capacity of the display buffer memory 65. In this case, since the memory capacity of the display buffer memory 65 is 512 KB which is equal to the number of scanning lines of the monitor 9 for displaying image data, the memory capacity of each of the image memories 63a to 63d is 256 KB.

Unless a defect is found, the image memories 63a to 63d store the A/D-converted image signals from the sensor cameras 3a to 3d in a scroll manner. In this case, the addresses of the image memories 63a to 63d are updated in the scroll manner by the address data output from a width-directional address counter 67 and a length-directional address counter 68, so that the digital image signals are stored in the image memories in the scroll manner.

When the defect is found by the defect detecting device 7, the write-in of image signals to the image memory 63a, for example, is stopped in response to the defect detection signal and completion of one line scanning, and at the same time the switch circuit 61 switches the image memory 63a to the image memory 63b to store image data of the remaining half of the frame. When the image memory 63b completely stores the image data of the remaining half frame, at first the image data stored in the image memory 63a corresponding to the sensor camera 3a by which a defect is scanned is transferred to the display buffer memory 65 through the bus line 64 and then the image data stored in the image memory 63b neighboring the image memory 63a is transferred thereto. In this transferring operation, in order to arrange a half defect on the central position of the screen, the addresses of the image memory 63a corresponding to the sensor camera 3a are designated in the sequential time order in which data is written into the memory 63a.

After the data transferring, the switch circuit 61 performs a switching operation so as to connect the sensor camera 3a to the corresponding image memory 63a via the A/D converter 62a.

The display buffer memory 65 synthesizes two half-frame image data transferred from the two image memories 63a and 63b and produces synthetic image data corresponding to a single frame. The synthetic image data is retained in the display buffer memory 65 unless a reset command is issued.

When image data is transferred from any one of the image memories 63a to 63d, the previous synthetic image data is rewritten to new image data. Where necessary, a window command is issued to the display buffer memory 65, whereby a center portion (indicated by a broken line in FIG. 11) of the synthetic image data, which includes the defect, can be cut out. The window function is preset at the time of initial setting operation.

The monitor 9 which receives the output from the display buffer memory 65 displays the synthetic image data as a still image on its screen. Needless to say, the monitor 9 is monitored by an operator on the basis of an alarm issued simultaneously with defect detection from an alarm device installed in the operator's room.

With the above structure, the sensor cameras 3a to 3d scan the surface of the object 1 over the entire width thereof, while the object 1 at the inspection position is illuminated by at least one of the lighting devices 5 and 6. Image signals from the sensor cameras 3a to 3d are input to the defect detecting device 7 for defect detection, as well as the defect image processing device 8. Thus, the image signals are A/D converted and input to the image memories 63a to 63d provided for the respective cameras 3a to 3d.

Since the lighting devices 5 and 6 and sensor cameras 3a to 3d are used for both defect detection and defect display (described later), consistency is ensured between the resolution of the lighting system for emphasizing and monitoring the defect and the resolution of the cameras. Thus, in the defect display, the defect is clearly displayed.

The defect display will now be described with reference to FIG. 11. For the purpose of simplicity, FIG. 11 shows only the sensor camera 3a, image memory 63a corresponding to the sensor camera 3a, image memory 63b adjacent to the image memory 63a, bus line 64, display buffer memory 65, and monitor 9. The image memory 63a stores A/D-converted image signals from the sensor camera 3a in a scroll manner. The memory capacity of the image memory 63a is half the capacity of the display buffer memory 65. When the camera 3a scan a defect and also the defect detecting device 7 detects the defect, the switch circuit 61 is operated by the timing controller 66 in response to the completion of one line scanning to disconnect the camera a from the corresponding image memory 63a and connect it to the image memory 63b neighboring the image memory 63a. Thus, the scroll writing operation of the image memory 63a is stopped, and the image memory 63a stores image data includes a half defect E1.

Subsequent image data output from the sensor camera 3a is input to the neighboring alternative image memory 63b which is selected by the switch circuit 61.

Just after the image memory 63b has stored image data corresponding to half the memory capacity of the display buffer memory 65 and including the other half defect E2, the image data stored in the image memories 63a and 63b are transferred sequentially to the buffer memory 65 via the bus line 64 while the data is rearranged in a time-basis manner.

Subsequently, the display buffer memory 65 synthesizes (rearranges) the image data transferred previously from the image memory 63a and the image data transferred from the image memory 63b. In the synthetic image, the half defect images E1 and E2 are combined to form the actual shape of the defect E. Thus, the position of the defect is always situated at a substantially central position of the synthetic image.

The display buffer memory 65 enables the monitor 9 to display the synthetic image as a still image. Thereby, the defect E can be displayed at the vertically middle point (i.e. the vertical ½ position) on the screen of the monitor 9.

Since the position of the detected defect E on the screen of the monitor 9 can be stabilized, the operator need not find out the defect E on the monitor screen. Thus, the visual recognition of the defect on the screen of the monitor 9 can be made easier.

In the above embodiment, when an image memory corresponding to a sensor camera scanning a defect and an image memory neighboring it have stored half-frame image data, respectively, the half-frame image data are transferred sequentially to a display buffer memory for storing image data of one frame. However, this image data transferring may be performed as follows.

When the camera 3a scans a defect, the defect detecting device 7 detects the defect, and the scroll writing operation of the image memory 63a is stopped, the image data including half defect E1 stored in the image memory 63a is transferred to the display buffer memory via the bus line 64, while the data is rearranged in a time-basis manner. Subsequent image signals output from the sensor camera 3a during the data transfer are input to the neighboring alternative image memory 63b. After the image memory 63b has stored data corresponding to half the memory capacity of the display buffer memory 65 and including the other half defect E2, the switch circuit 61 is restored to its initial state and the image data stored in the image memory 63b is transferred to the buffer memory 65 via the bus line 64 while the data is rearranged in a time-basis manner. The display buffer memory 65 synthesizes the image data transferred previously from the image memory 63a and the image data transferred from the image memory 63b, whereby the half defect images E1 and E2 are combined to form the actual shape of the defect E.

As has been described above, in the defect display apparatus with the above structure, image signals from the sensor cameras 3a to 3d for scanning a printed sheet, or a solid-color sheet (a sheet without a pattern) are supplied to a defect detecting device for detecting a print defect from the printed sheet or a defect including a spot, stain or smudge from the solid-color sheet. The image data are supplied to and processed by a plurality of image memories 63a to 63d and the display memory buffer 65, so that the defect is displayed on the screen of the monitor 9. Thus, a monitor color TV camera and a driving mechanism therefor, which have been required in the prior art in addition to the sensor cameras 3a to 3d, can be dispensed with. As a result, the mechanical parts of the defect display system are arranged only at the inspection position. Therefore, the space for installation of the system can be saved, and the system can advantageously be provided in the inspection line.

The cameras need not be moved in the width direction of the to-be-recognized object. Thus, when defects on the object are close to each other and the detection of the defects is continuous, it is possible to prevent an undesirable situation from arising, in which the cameras are not timely moved and the monitor screen fails to display the defect. In addition, the inspection line speed can easily be increased.

As has been described above in detail, the defect can be displayed by utilizing the image signals obtained by the sensor cameras while the object is illuminated by the lighting devices for defect detection. Thus, there is consistency between the resolution of the lighting system and the resolution of the cameras, and therefore the detected defect can be clearly displayed on the monitor and the defect display performance can be enhanced. Furthermore, since the defect is displayed at the vertically middle point (½ height position) on the monitor screen, the defect display position is stabilized and the defect can easily be found on the monitor screen.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A method of displaying a defect appearing on an object having a surface which is conveyed in one direction, said method comprising the steps of:

optically scanning the object in the width direction thereof, and obtaining object image data corresponding to the surface of the object;

detecting a defect in the object by processing the object image data;

writing the object image data in a memory in a scroll manner;

stopping the writing of the object image data in response to the detection of the defect, and retaining the object image data including the defect as still image data;

displaying the still image data read out from the memory on a monitor screen as a still image such that the defect is displayed at a predetermined fixed vertical position on the monitor screen;

wherein said data writing step includes a step of storing half-frame image data corresponding to at least a half frame;

said data retaining step includes a step of stopping the writing in response to the detection of the defect and retaining the half-frame image data in the memory as still image data, and a step of writing the other half-frame image data in another memory; and said displaying step includes a step of combining both half-frame image data to produce one-frame image data corresponding to one frame containing the defect at a central area thereof, and a step of displaying the produced one-frame image data on the monitor screen as a still image containing the defect at a central area thereof or a vertical middle position thereof.

2. A method of displaying a defect appearing on an object having a surface which is conveyed in one direction, said method comprising the steps of:

optically scanning the object in the width direction thereof, and obtaining object image data corresponding to the surface of the object;

detecting a defect in the object by processing the object image data;

writing the object image data in a memory in a scroll manner;

stopping the writing of the object image data in response to the detection of the defect, and retaining the object image data including the defect as still image data;

displaying the still image data read out from the memory on a monitor screen as a still image such that the defect is displayed at a predetermined fixed vertical position on the monitor screen;

wherein a plurality of sensor cameras are arranged along the width direction of the object for obtaining an image of the object, and wherein, said storing step includes a step of writing a plurality of image data obtained by said sensor cameras in a plurality of image memories;

said defect detecting step includes a step of detecting a defect from the image data;

said data retaining step includes a step of stopping the writing in the image memory corresponding to the sensor camera, which outputs image data containing the defect, in response to the detection of the defect, and retaining, the image data of a first half of one frame in the image memory, and a step of writing the image data of a second half of the frame in another image memory; and said displaying step includes a step of writing in a display image memory the image data of the first half of the frame and the image data of the second half of the frame as one-frame image data, and a step of displaying the one-frame image data read out from the display image memory on the monitor screen as a still image containing the defect.

3. The method according to claim 1, wherein said detecting step includes a step of extracting a defect image signal corresponding to a defect from the object image data and a step of recognizing the defect when the defect image signal exceeds a predetermined signal level and parameters corresponding to a predetermined width and a predetermined length.

4. An apparatus for displaying a defect appearing on an object having a surface which is conveyed in one direction, said apparatus comprising:

image sensing means for scanning the object in the width direction thereof, and outputting object image data corresponding to the object;

defect detecting means for processing the object image data, to detect a defect in the object, and outputting a defect detection signal;

memory means for storing the object image data in a scroll manner;

retaining means for Stopping the storing of the object image data in response to the defect detection means, and retaining the object image data including the defect in said memory means as still image data;

displaying means for displaying the still image data read out from the memory means on a monitor screen as a still image such that the defect is displayed at a predetermined fixed vertical position on the monitor screen;

wherein said memory means includes a plurality of image memories each having the memory capacity for storing half-frame image data corresponding to at least a half frame;

said retaining means includes storing means for stopping the storing in response to said defect detection signal, retaining the half-frame image data in one of said image memories as still image data, and writing the other half-frame image data in another image memory; and said displaying means includes means for combining both half-frame image data to produce one-frame image data corresponding to one frame containing the defect at a central area of the one-frame image data and means for displaying the produced one-frame image data on the monitor screen as a still image containing the defect at a central area or a vertical middle position thereof.

5. An apparatus for displaying a defect appearing on an object having a surface which is conveyed in one direction, Said apparatus comprising:

image sensing means for scanning the object in the width direction thereof and outputting object image data corresponding to the object;

defect detecting means for processing the object image data, to detect a defect in the object, and outputting a defect detection signal;

memory means for storing the object image data in a scroll manner;

retaining means for stopping the storing of the object image data in response to the defect detection means, and retaining the object image data including the defect in said memory means as still image data;

displaying means for displaying the still image data read out from the memory means on a monitor screen as a still image such that the defect is displayed at a predetermined fixed vertical position on the monitor screen;

wherein said image sensing means includes a plurality of sensor cameras arranged in the width direction of the object;

said memory means includes a plurality of image memories for storing image data obtained by said sensor cameras in a scroll manner;

said defect detecting means includes means for detecting a defect from the image data;

said retaining means includes means for stopping the storing the image data in the image memory corresponding to the sensor camera, which outputs image data containing the defect, in response to the defect detection signal, and retaining image data of a first half of one frame in the image memory, and means for storing image data of a second half of the frame in another image memory; and said displaying means includes a display memory for storing the image data of the first half of the frame and the image data of the second half of the frame as one-frame image data, and monitor means for displaying the one-frame image data read out from the display image memory as a still image containing the defect at a vertical middle position on a monitor screen.

6. The apparatus according to claim 4, wherein said defect detecting means includes means for extracting a defect image signal corresponding to a defect from the object image data and means for outputting the defect detection signal when the defect image signal exceeds a predetermined signal level and parameters corresponding to a predetermined width and a predetermined length.

7. An apparatus for displaying a defect appearing on an object having a surface which is conveyed in one direction, said apparatus comprising:

sensor cameras arranged in the width direction of the object for scanning the surface of the object and outputting object image data units;

defect detecting means having memory means storing reference image data for comparing the object image data with the reference image data, and outputting a defect detection signal;

image processing means including a plurality of image memories provided for the respective sensor cameras for storing the object image data units, and means for stopping storing the image data in the image memory corresponding to the sensor camera which has scanned the surface containing the defect, in response to the defect detection signal, and retaining the object image data containing the defect in the image memory as still image data;

displaying means for displaying the still image data read out from the image memory as a still image such that the defect is displayed at a predetermined fixed vertical position on the monitor screen;

wherein each of said image memories has a memory capacity for storing image data corresponding to a half frame;

said displaying means includes a display memory having a memory capacity for storing image data of one frame; and said image processing means includes means for storing image data of a first-half frame in the image memory corresponding to the sensor camera, which has scanned the pattern containing the defect, in response to the defect detection signal, means for storing image data of a second-half frame in one of the image memories which differs from the image memory storing the data of the first-half frame, and means for transferring the data of the first and second half frames stored in said image memories to the display memory and creating one-frame image data in the display memory.

8. The apparatus according to claim 7, further comprising lighting means for selectively illuminating at least one of front and rear surfaces of the object in accordance with the kind of material of the object.

9. The apparatus according to claim 7, wherein said defect detecting means includes short-defect detecting means for detecting a missing pattern as a defect and splashing defect detecting means for detecting a pattern including at least one undesirable pattern as a defect.

10. The apparatus according to claim 7, wherein said image memories are constituted by a memory device having memory areas assigned to these image memories.

11. The apparatus according to claim 7, wherein said image processing means includes switch circuit means for supplying image data output from the sensor camera which has scanned the surface of the object containing the defect to one of the image memories which differs from the image memory which stores the still image data and corresponds to the sensor camera.

12. The apparatus according to claim 7, wherein said displaying means includes a monitor which receives the image data readout from the display image memory and displays the still image such that the defect is displayed at a center point on the screen of the monitor.

13. The apparatus according to claim 7, wherein said object is a printed matter on which at least one pattern is printed.

14. The apparatus according to claim 7, wherein said object includes a sheet matter without a pattern.

* * * * *